(12) United States Patent
Bastings et al.

(10) Patent No.: US 10,815,176 B2
(45) Date of Patent: Oct. 27, 2020

(54) HEAT INTEGRATION IN A PROCESS FOR THE PREPARATION OF ETHYLENE CARBONATE AND ETHYLENE GLYCOL

(71) Applicant: SHELL OIL COMPANY, Houston, TX (US)

(72) Inventors: Roel Guillaume Hubertus Leonardus Bastings, Amsterdam (NL); Vesna Bojovic, Ras Laffan (QA); Alexandre Molina, Moerdijk (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/613,646

(22) PCT Filed: May 17, 2018

(86) PCT No.: PCT/EP2018/062910
§ 371 (c)(1),
(2) Date: Nov. 14, 2019

(87) PCT Pub. No.: WO2018/211013
PCT Pub. Date: Nov. 22, 2018

(65) Prior Publication Data
US 2020/0079712 A1 Mar. 12, 2020

(30) Foreign Application Priority Data
May 19, 2017 (EP) .................................... 17171869

(51) Int. Cl.
| | | |
|---|---|---|
| *C07C 29/78* | (2006.01) |
| *B01D 3/00* | (2006.01) |
| *B01D 5/00* | (2006.01) |
| *B01D 3/14* | (2006.01) |
| *B01D 53/14* | (2006.01) |
| *B01D 53/18* | (2006.01) |
| *B01J 8/00* | (2006.01) |
| *B01J 8/04* | (2006.01) |

(52) U.S. Cl.
CPC .............. *C07C 29/78* (2013.01); *B01D 3/143* (2013.01); *B01D 5/006* (2013.01); *B01D 5/0039* (2013.01); *B01D 53/1487* (2013.01); *B01D 53/18* (2013.01); *B01J 8/0015* (2013.01); *B01J 8/0492* (2013.01); *B01J 2208/0053* (2013.01); *B01J 2208/00176* (2013.01)

(58) Field of Classification Search
CPC ...... C07C 29/78; B01D 3/143; B01D 5/0039; B01D 5/006; B01D 53/18
See application file for complete search history.

(56) References Cited

FOREIGN PATENT DOCUMENTS

| EP | 0776890 A2 | 6/1997 |
|---|---|---|
| EP | 2155375 A2 | 2/2010 |
| GB | 2107712 A | 5/1983 |
| WO | 2009021830 A1 | 2/2009 |
| WO | 2009140318 A1 | 11/2009 |
| WO | 2009140319 A1 | 11/2009 |
| WO | 2016046100 A1 | 3/2016 |
| WO | 2017102706 A1 | 6/2017 |

OTHER PUBLICATIONS

International Search Report and Written Opinion received for PCT Patent Application No. PCT/EP2018/062910, dated Jul. 12, 2018, 8 pages.
Brunauer et al., "Adsorption of Gases in Multimolecular Layers", Journal of the American Chemical Society, vol. 60, Feb. 1938, pp. 309-316.

*Primary Examiner* — Sikarl A Witherspoon (57) ABSTRACT

Processes and associated reaction systems for the preparation of ethylene carbonate and ethylene glycol from ethylene oxide are provided, particularly processes and associated reaction systems directed to heat integration in the treatment of recycle gas streams.

15 Claims, 2 Drawing Sheets

HEAT INTEGRATION IN A PROCESS FOR THE PREPARATION OF ETHYLENE CARBONATE AND ETHYLENE GLYCOL

CROSS REFERENCE TO RELATED APPLICATIONS

This is a national stage application of International Application No. PCT/EP2018/062910, filed 17 May 2018, which claims benefit of priority to European Patent Application No. 17171869.5, filed 19 May 2017.

FIELD OF THE INVENTION

The present invention relates to processes and systems for the preparation of ethylene carbonate and ethylene glycol from ethylene oxide, in particular to heat integration in the treatment of recycle gas streams.

BACKGROUND OF THE INVENTION

Ethylene glycol (EG) is a valuable industrial compound that is widely employed as starting material for the manufacture of polyester fibers and polyethylene terephthalate (PET) resins; it also finds application in automotive anti-freeze and hydraulic brake fluids, aircraft de-icers as well as in pharmaceutical products.

Ethylene glycol is normally prepared from ethylene oxide (EO), which is in turn prepared by silver-catalyzed oxidation of ethylene. More specifically, ethylene and oxygen are passed over a silver oxide catalyst, typically at pressures of 10-30 bar and temperatures of 200-300oC, producing a product stream comprising ethylene oxide, carbon dioxide, ethylene, oxygen and water. In one well-known process, the ethylene oxide is then reacted with a large excess of water in a non-catalytic process, producing a glycol product stream comprising close to 90 wt % monoethylene glycol (MEG), the remainder being predominantly diethylene glycol (DEG), some triethylene glycol (TEG) and a small amount of higher homologues. In another well-known process, ethylene oxide is reacted with carbon dioxide in the presence of a catalyst to produce ethylene carbonate. The ethylene carbonate is subsequently hydrolyzed to provide ethylene glycol. Reaction via ethylene carbonate significantly improves the selectivity of ethylene oxide conversion to monoethylene glycol.

In the last few decades, many efforts have been directed towards the development of simplified processes and equipment for producing alkylene glycols from alkylenes, notably ethylene glycol from ethylene. For example, GB2107712 describes a process for preparing monoethylene glycol wherein the gases from the ethylene oxide (EO) reactor are supplied directly to a reactor wherein ethylene oxide is converted to ethylene carbonate or to a mixture of ethylene glycol and ethylene carbonate.

EP 0776890 describes a process wherein the gases from the ethylene epoxidation reactor are supplied to an absorber, wherein the absorbing solution mainly contains ethylene carbonate (EC) and ethylene glycol (EG). The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a separate hydrolysis reactor and subjected to hydrolysis in the presence of a hydrolysis catalyst.

EP2178815 describes a reactive absorption process for preparing monoethylene glycol, wherein the gases from the ethylene epoxidation reactor are supplied to a reactive absorber and the ethylene oxide is contacted with an aqueous lean absorbent in the presence of one or more carboxylation and hydrolysis catalysts, and wherein the majority of the ethylene oxide is converted to ethylene carbonate (EC) or ethylene glycol (EG) in the absorber.

In each of these instances, a gas stream containing gases that are not absorbed by the recirculating absorbent stream will be produced from the ethylene oxide absorber or reactive absorber. This gas stream is removed at or near the top of the absorber as an ethylene oxide absorber overhead stream typically comprising unreacted reactants (e.g., ethylene and oxygen), ballast gas (e.g., methane), carbon dioxide, etc.

The ethylene oxide absorber overhead stream is generally at least partially treated in a carbon dioxide removal section and then recombined with any gases bypassing the carbon dioxide removal section. The combined gases are then, after compression, at least partially recycled as recycle gas stream to the ethylene oxide reactor.

However, it has been found that in those processes where the carboxylation reaction is performed in the absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based catalysts commonly employed in the conversion (epoxidation) of ethylene to ethylene oxide are very susceptible to catalyst poisoning, in particular poisoning by gaseous iodide-containing impurities, such as such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst.

Accordingly, it is desirable to remove such catalyst poisons as much as is practicable from the recycle gas stream before it comes into contact with the epoxidation catalyst. To this end, the application of one or more so-called "guard bed" systems positioned upstream of the EO reactor, as previously disclosed in, among others, EP2285795, EP2279182 and EP2155375 has been developed. Such guard bed systems typically comprise one or more guard bed vessels, each guard bed vessel comprising an inlet, an outlet and a packed bed ("guard bed") comprising an absorbent ("guard bed material") capable of reducing the quantity of iodide-containing impurities in a gaseous stream by chemical or physical means including, but not limited to, reaction with the impurities and absorption of the impurities.

It is known that the presence of water at significantly high concentration in the recycle gas stream brought into contact with a guard bed negatively affects the absorption capacity of the guard bed material. Therefore, the ethylene oxide absorber overhead stream is typically cooled to a temperature in the range of about 15 to 50° C. to condense and separate water from the gaseous stream overhead stream. In this way the water concentration in the recycle gas stream supplied to the one or more guard bed systems is reduced. Moreover, evaporated glycols from the ethylene oxide absorber are condensed and recovered as well, and circulated back with the condensed water to the ethylene oxide absorber. Additionally, cooling of the recycle gas stream before compression reduces energy consumption by the compressor and facilitates selection of suitable compressor materials.

In order to maximize the absorption capacity of guard bed materials suitable for removing impurities from a recycle gas stream, guard bed systems are operated at elevated temperatures, typically in the range of 65 to 145° C., depending on the impurities to be removed and the guard bed material used. Therefore, the cooled ethylene oxide absorber overhead stream needs to be heated again to the preferred operating temperature of the first guard bed system located downstream of the ethylene oxide absorber overhead condenser.

Heating (and optionally subsequent cooling) of the gaseous feeds stream of the one or more guard bed systems to the optimal guard bed operating temperature may be realized by a variety of heater and cooler equipment, typically including the import of external steam and cooling water. However, each additional heating and cooling device included in the ethylene glycol manufacturing plant will negatively affect overall capital and operating expenditure.

Accordingly, the present inventors have sought to provide improved processes and systems suitable for the production of ethylene carbonate and/or ethylene glycol. In particular, the present inventors have sought to provide processes and systems that reduce the amount of impurities in a gaseous process stream so that it may be recycled in the production of ethylene carbonate and/or ethylene glycol and have further sought to reduce the energy consumption associated therewith.

SUMMARY OF THE INVENTION

Accordingly, in one aspect there is provided a process comprising supplying an ethylene oxide absorber overhead stream to an ethylene oxide absorber overhead condenser to produce a cooled recycle gas stream and one or more aqueous streams, heating at least a portion of said cooled recycle gas stream to provide a heated recycle gas stream, contacting said heated recycle gas stream with one or more guard bed materials in one or more guard bed systems positioned upstream of an ethylene oxide reactor to provide a treated recycle gas stream, contacting an epoxidation feed gas comprising ethylene, oxygen and at least a portion of said treated recycle gas stream with an epoxidation catalyst in ethylene oxide reactor to yield an epoxidation reaction product stream, contacting the epoxidation reaction product stream in an ethylene oxide absorber with a lean absorbent stream in the presence of a carboxylation and hydrolysis catalyst to yield a fat absorbent stream comprising ethylene carbonate and/or ethylene glycol and an ethylene oxide absorber overhead stream, wherein the cooled recycle gas stream is heated by heat exchange with a hot process streams selected from (i) the ethylene oxide absorber overhead stream in the ethylene oxide absorber overhead condenser; (ii) steam produced in an ethylene glycol purification column overhead condenser, in a first heat exchanger located downstream of the ethylene oxide absorber overhead condenser; and (iii) steam produced by flashing one or more condensate streams collected in the process, in a second heat exchanger located downstream of the ethylene oxide absorber overhead condenser, or a combination thereof.

Further, in accordance with another aspect there is provided reaction system for the production of ethylene carbonate and/or ethylene glycol comprising (i) a recycle gas loop fluidly connected to a source of ethylene and oxygen;

(ii) an ethylene oxide reactor comprising an epoxidation catalyst, an inlet, and an outlet, wherein the inlet of the ethylene oxide reactor is fluidly connected to the recycle gas loop;

(iii) an ethylene oxide absorber configured to produce an ethylene oxide absorber overhead stream and a fat absorbent stream comprising ethylene carbonate and/or ethylene glycol, said ethylene oxide absorber comprising a carboxylation and hydrolysis catalyst, an inlet fluidly connected to the outlet of the ethylene oxide reactor, an inlet for lean absorbent, an outlet for discharging a recycle gas stream and an outlet for discharging a fat absorbent stream;

(iv) an ethylene oxide absorber overhead condenser configured to produce a recycle gas stream and a condensate stream, said ethylene oxide absorber overhead condenser comprising an inlet fluidly connected to the outlet of the ethylene oxide absorber for discharging a recycle gas stream, an inlet for receiving a cooled recycle gas stream, an outlet fluidly connected to the recycle gas loop, and an outlet for discharging a cooled recycle gas stream;

(v) a finishing reactor configured to produce an ethylene glycol stream, comprising an inlet fluidly connected to the outlet of the ethylene oxide absorber for discharging a fat absorbent stream, and an outlet for discharging an ethylene glycol stream;

(vi) a dehydrator configured to produce a concentrated ethylene glycol stream comprising an inlet and an outlet, comprising an inlet fluidly connected to the outlet for discharging an ethylene glycol stream from the finishing reactor, and an outlet for discharging a concentrated ethylene glycol stream;

(vii) an ethylene glycol purification column equipped with an ethylene glycol purification column overhead condenser, an inlet fluidly connected to outlet of the dehydrator for discharging a concentrated ethylene glycol stream, an outlet for discharging a condensate stream, and an outlet for discharging a steam stream, (viii) one or more guard bed systems comprising an inlet, an outlet and one or more guard bed vessels comprising one or more guard bed materials, wherein the inlet of the guard bed system is fluidly connected to the recycle gas loop, wherein the one or more guard bed materials are configured to remove at least a portion of one or more impurities from the recycle gas stream to yield a treated recycle gas stream; and wherein the outlet of the guard bed system is fluidly connected to the recycle gas loop;

(ix) one or more guard bed heaters located upstream of the one or more guard bed systems, comprising an inlet for receiving a recycle gas stream and outlet for discharging a heated recycle gas stream, wherein the one or more guard bed heaters are fluidly connected with the outlet of the ethylene glycol purification column overhead condenser for discharging a steam stream and/or with the steam outlet of a condensate flash vessel.

DETAILED DESCRIPTION

Described herein are processes and systems for the production of ethylene carbonate and/or ethylene glycol. By using the processes and systems disclosed herein, it is possible to utilize the heat generated in one or more selected parts in the process to heat up colder feed streams for other parts, thereby allowing a significant part of the thermal energy generated in the production of ethylene glycol to be recovered and utilized in that same process. More specifically, by employing particular combinations of heat exchangers and heaters consuming low- and medium-pressure steam generated in the ethylene glycol process and directly contacting hot and cold process streams, it is possible to substantially reduce the amount of external thermal energy to be provided to the process, and even for the process to become an exporter of high-pressure steam.

Accordingly, the systems and processes disclosed herein provide the advantage that thermal energy is effectively recovered and utilized in appropriate parts of the process, thereby reducing operating costs. Additionally, such heat integration may reduce the heat transfer surface of existing process equipment, thereby allowing reducing its size, thus further contributing to reducing capital costs.

The process of producing ethylene glycol and/or ethylene carbonate by epoxidation of ethylene and reactive absorption of ethylene oxide has been described in detail in, among others, WO2009021830, WO2009140318, WO2009140319, the disclosures of which are hereby incorporated by reference.

Typically, the epoxidation process comprises reacting, in an ethylene oxide reactor, ethylene with oxygen in the presence of an epoxidation catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane (ethyl chloride), vinyl chloride or dichloroethane, may be supplied for ethylene oxide catalyst performance control.

The ethylene oxide reactor is typically a multitubular, fixed bed reactor. The epoxidation catalyst preferably comprises silver and optionally promoter metals deposited on a support material, for example, alumina. The epoxidation reaction is preferably carried out at pressures of greater than 1 MPa and less than 3 MPa and temperatures of greater than 200° C. and less than 300° C. The ethylene oxide product stream withdrawn from the ethylene oxide reactor is preferably cooled in one or more coolers, preferably with generation of steam at one or more pressure and temperature levels.

The ethylene oxide product stream from the ethylene oxide reactor, which typically comprises ethylene oxide, unreacted reactants (i.e., ethylene and oxygen), carbon dioxide, and water, may then be passed to an absorber in which it is intimately contacted with lean absorbent.

Typically, the lean absorbent comprises at least 20 wt % water, and preferably comprises from 20 wt % to 80 wt % water. The lean absorbent may also comprise ethylene glycol.

In the absorber, the ethylene oxide product stream is intimately contacted with the lean absorbent in the presence of one or more carboxylation and hydrolysis catalysts. If this occurs in the presence of only one catalyst, then the catalyst must promote carboxylation and hydrolysis. If this occurs in the presence of two or more catalysts, then each catalyst can promote carboxylation or hydrolysis or can promote both reactions (provided that at least one catalyst promotes carboxylation and at least one catalyst promotes hydrolysis). Preferably, the ethylene oxide product stream is contacted with lean absorbent in the presence of at least two catalysts including a first catalyst that promotes carboxylation and a second catalyst that promotes hydrolysis. Suitably, the absorber may be the sort of reactive absorber described in WO2009021830 or in co-pending application PCT/EP2015/071534.

Preferably, the one or more carboxylation and hydrolysis catalysts is/are homogenous, and the lean absorbent contains the one or more catalysts. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide.

Homogeneous catalysts that are known to promote hydrolysis include basic alkali metal salts such as potassium carbonate, potassium hydroxide and potassium bicarbonate, or alkali metal metalates such as potassium molybdate.

Preferred homogeneous catalyst systems include a combination of potassium iodide and potassium carbonate, and a combination of potassium iodide and potassium molybdate.

In another embodiment, the one or more carboxylation and hydrolysis catalysts is/are heterogeneous and the heterogeneous catalyst(s) is/are contained in vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilized on solid supports containing quaternary ammonium or quaternary phosphonium groups, such as ion exchange resins containing quaternary ammonium or quaternary phosphonium groups. Heterogeneous catalysts that promote hydrolysis include metalates immobilized on solid supports, for example molybdates, vanadates or tungstates immobilized on ion exchange resins containing quaternary ammonium or quaternary phosphonium groups, or basic anions such as bicarbonate ions immobilized on solid supports, for example bicarbonate immobilized on ion exchange resins containing quaternary ammonium or quaternary phosphonium groups.

The temperature in the absorber is preferably from 50° C. to 160° C., preferably from 80° C. to 150° C., more preferably from 80° C. to 120° C. This is higher than the temperature in an absorber in a conventional process and is required to promote the carboxylation and hydrolysis reactions.

Temperature higher than 160° C. is not preferred as this may reduce the selectivity of ethylene oxide conversion to ethylene glycol. Both the ethylene oxide product stream and the lean absorbent are preferably supplied to the absorber at temperatures in the range from 50° C. to 160° C.

The pressure in the absorber is from 1 to 4 MPa, preferably from 2 to 3 MPa. The preferred pressure is a compromise between lower pressures that require less expensive equipment (e.g. equipment having thinner walls) and higher pressures that increase absorption and reduce the volumetric flow of the gas, thereby reducing the size of equipment and piping.

Preferably, at least 50% of the ethylene oxide entering the absorber is converted in the absorber. Preferably, at least 60%, more preferably at least 70%, even more preferably at least 80%, most preferably at least 90% of the ethylene oxide entering the absorber is converted in absorber. The ethylene oxide may undergo carboxylation, providing ethylene carbonate. The ethylene oxide may undergo hydrolysis, providing ethylene glycol.

Additionally, the ethylene carbonate that is produced from the ethylene oxide may undergo hydrolysis, providing ethylene glycol.

The ethylene oxide product stream supplied to the absorber comprises carbon dioxide. However, it is possible that the ethylene oxide product stream may contain insufficient carbon dioxide to achieve desired levels of carboxylation. Optionally, an additional source of carbon dioxide is supplied to the absorber, e.g. recycle carbon dioxide from a finishing reactor, carbon dioxide from recovered from a carbon dioxide removal section downstream of the absorber and/or, for example at start-up, carbon dioxide from an external source.

In accordance with the present disclosure, the ethylene oxide absorber overhead stream, which typically has a temperature in the range of 90-130° C., is then supplied to a condenser. Typically, in order to achieve the desired degree of cooling of the hot ethylene oxide absorber overhead stream, the ethylene oxide absorber overhead stream is supplied to at least a first and a second condenser in series. In one embodiment, the ethylene oxide absorber overhead stream is supplied to a first condenser, such as a shell-and-tube heat exchanger, to produce a dewatered recycle gas stream and an aqueous stream. Preferably, the dewatered recycle gas stream is subsequently supplied to a second condenser, such as a cooling water heat exchanger, to produce a further dewatered and cooled recycle gas stream.

Thus, in one embodiment, the ethylene oxide absorber overhead stream is provided to a first condenser to produce a dewatered recycle gas stream and an aqueous stream, wherein the dewatered recycle gas stream is supplied to a second condenser to produce a further dewatered and cooled recycle gas stream, and wherein said recycle gas stream is supplied to a vapor-liquid separator to produce a cooled and dehydrated recycle gas stream.

Said vapor-liquid separator may for example be a knock-out vessel, or an absorber knock-out column including a wash section.

In some embodiments, the aqueous stream withdrawn from the vapour-liquid separator may be supplied to a distillation apparatus to yield an overhead impurities stream and a purified aqueous process stream, wherein at least a portion of the purified aqueous process stream is supplied to the ethylene oxide absorber.

In some embodiments, the ethylene oxide absorber may be temporarily by-passed. In such case, a gaseous process stream may be directly withdrawn as effluent from the ethylene oxide reactor, typically after pre-cooling in one or more epoxidation product coolers downstream of the ethylene oxide reactor, and provided to the one or more condensers to provide a cooled recycle gas stream. Generally, a recycle gas compressor is located in the recycle gas loop, preferably downstream of the last condenser in line, in order to expose the recycle gas compressor to the lowest feed temperature and dew point. A preferable operating pressure in the gas loop is in the range of from 1 to 4 MPa (gauge). A more preferable operating pressure is in the range of from 1.5 to 3 MPa (gauge).

A 'fat absorbent' stream is withdrawn from the absorber, preferably by withdrawing liquid from the bottom of the absorber. The fat absorbent stream will comprise ethylene carbonate and/or ethylene glycol and any remaining ethylene oxide, if present, depending on the conditions, set-up and catalyst in the absorber. In addition, when the one or more carboxylation and hydrolysis catalysts is/are homogenous, the fat absorbent stream will further comprise the one or more carboxylation and hydrolysis catalysts.

Optionally, a portion or all of the fat absorbent stream exiting the ethylene oxide absorber is supplied to one or more finishing reactors (e.g., to provide further conversion of any ethylene oxide and/or ethylene carbonate that was not converted to ethylene glycol in the absorber). Suitable finishing reactors may include a carboxylation reactor, a hydrolysis reactor, a carboxylation and hydrolysis reactor, and a combination thereof. Supply to one or more finishing reactors is preferred if a significant quantity (e.g. at least 1%) of ethylene oxide or ethylene carbonate is not converted to ethylene glycol in the absorber.

Preferably, the one or more finishing reactors comprise at least a hydrolysis reactor.

Carbon dioxide may be produced in the one or more finishing reactors and, if desired, may be separated from the one or more finishing reactor product stream(s) as it leaves the one or more finishing reactors and is optionally recycled to the absorber.

The temperature in the one or more finishing reactors is typically from 100° C. to 200° C., preferably from 100° C. to 180° C. The pressure in the one or more finishing reactors is typically from 0.1 to 3 MPa (gauge).

In one embodiment, at least a portion of the ethylene glycol produced in the ethylene oxide absorber and/or at least a portion of the ethylene glycol produced in the finishing reactor(s) is supplied to one or more dehydrators to provide a concentrated ethylene glycol stream.

The dehydrator is preferably one or more columns, including at least one vacuum column, preferably operating at a pressure of less than 0.05 MPa, more preferably less than 0.025 MPa and most preferably about 0.0125 MPa.

In one embodiment, at least a portion of the concentrated ethylene glycol stream is supplied to an ethylene glycol purification column, from which a purified ethylene glycol product stream is withdrawn. Additionally, a vaporous overhead stream is produced, which is supplied to an overhead condenser to produce a condensate stream and steam.

In a preferred embodiment, at least a portion of the fat absorbent stream comprising ethylene carbonate and/or ethylene glycol is supplied to one or more finishing reactors and/or one or more dehydrators to provide a concentrated ethylene glycol stream, and at least a portion of said concentrated ethylene glycol stream is supplied to an ethylene glycol purification column to produce a purified ethylene glycol product stream and a vaporous overhead stream, wherein said vaporous overhead stream is supplied to an ethylene glycol purification column overhead condenser to produce a condensate stream and steam.

After being supplied to the one or more condensers and optionally after further water removal, the temperature of the thus cooled recycle gas stream needs to be increased to the preferred operating temperature range of the one or more guard bed systems employed to remove impurities from the recycle gas stream, before being contacted with the epoxidation catalyst in the epoxidation reactor. For example, a guard bed system comprising a guard bed material capable of removing one or more alkyl iodide impurities from a recycle gas stream typically has a preferred operating temperature in the range of 80 to 145° C. Preferably, the one or more guard bed vessels in a guard bed system comprising a guard bed material capable of removing one or more alkyl iodide impurities from a recycle gas stream are operated at a temperature of at least 100° C., even more preferably at least at least 115° C., most preferably at least 120 ° C. Further, the one or more guard bed vessels in a guard bed system comprising a guard bed material capable of removing one or more alkyl iodide impurities from a recycle gas stream are preferably operated at a temperature of at most 140° C., most preferably at most 135° C., or from 100° C. to 145° C., or from 115° C. to 140° C. Preferably, they are operated in a temperature range from 120° C. to 135° C.

As a further example, a guard bed system comprising one or more guard bed vessels comprising a guard bed material capable of removing a vinyl iodide impurity from a recycle gas stream typically has a preferred operating temperature in the range of 65 to 95° C. Preferably, such guard bed vessels in a guard bed system capable of removing a vinyl iodide impurity from a recycle gas stream are operated at a temperature of at least 70° C., most preferably at least 83° C. Further, such guard bed vessels in a guard bed system capable of removing a vinyl iodide impurity from a recycle gas stream are preferably operated at a temperature of at most 90° C., most preferably at most 87° C., or from 65° C. to 95° C., or from 70° C. to 90° C., or from 83° C. to 87° C.

Thus, in accordance with the present disclosure, at least a portion, and preferably all, of the cooled recycle gas stream is heated before being supplied to a guard bed system located downstream of the ethylene oxide absorber and the one or more condensers. In further accordance with the present disclosure, the cooled recycle gas stream is heated by heat exchange with one or more hot process streams, wherein said hot process streams comprise one or more of (i) the ethylene oxide absorber overhead stream, (ii) steam produced by an ethylene glycol purification column overhead condenser and (iii) steam produced by flashing one or more condensate streams collected in the process.

Preferably, the cooled recycle gas stream is heated by subsequent heat exchange with the ethylene oxide absorber overhead stream and heat exchange with steam streams produced in the process. Preferably, the latter is accomplished using low-pressure steam produced by the ethylene glycol purification column overhead condenser followed by using steam produced by flashing one or more condensate streams collected in the process. This sequence of heat exchange with process streams of increasing temperature allows maximum integration of heat produced in various parts of the present process, wherein the maximum temperature increase per step is limited by the minimum allowable temperature approach between hot and cold side or the availability of steam.

Heat exchange with the ethylene oxide absorber overhead stream can be realized by counter-currently contacting the cooled recycle stream with the hot ethylene oxide absorber overhead stream in the first condenser located downstream of said ethylene oxide absorber. Typically, this will heat up the recycle gas stream to a temperature in the range of 70 to 125° C.

In one embodiment, this heated stream may be further heated by a primary guard bed heat exchanger, preferably using steam produced by the ethylene glycol purification column overhead condenser. The steam produced by the ethylene glycol purification column overhead condenser is low-pressure steam, typically having a pressure in the range of 1.5-3 kg/cm$^2$ gauge (g) [0.15-0.29 MPa gauge], preferably 1.5-2.5 kg/cm$^2$ (g) [0.15-0.25 MPa (g)]. This steam stream may be used to heat up, after pre-heating with the ethylene oxide absorber overhead stream, the recycle gas stream to a temperature that is typically in the range of 90 to 130° C., preferably 110 to 125° C.

In one embodiment, the thus heated recycle gas stream may be further heated to the desired (first) guard bed operating temperature by means of a secondary guard bed heat exchanger. Preferably, this secondary guard bed heater uses steam produced by flashing (pressure reduction) of the condensate streams collected from (higher-pressure) steam users in the process, thus allowing utilization of thermal energy contained in the discharged condensate(s). Typically, this is accomplished by collecting all or substantially all condensate streams discharged from steam-driven heaters and reboilers in the process and reducing the pressure (in a condensate flash vessel) of the collected condensates to a sufficiently low pressure to produce maximum steam of sufficiently high temperature for selected heat consumers in the process. In the process as described herein, this flash steam stream will typically have a pressure in the range of 2.5-3.5 kg/cm$^2$ g [0.25-0.34 MPa gauge], and may be used in a secondary guard bed heat exchanger to further heat up the recycle gas stream, if desired, to a temperature in the range of 110-145° C., preferably 120 to 135° C., before being contacted with a guard bed in a guard bed system. Accordingly, in a preferred embodiment, the cooled recycle gas stream is heated by subsequent heat exchange with the ethylene oxide absorber overhead stream in condenser; steam produced in an ethylene glycol purification column overhead condenser; and steam produced by flashing one or more condensate streams collected in the process.

Although the benefits of the present invention are most pronounced using this sequence of primary and secondary guard bed heaters with increasing steam pressure and heat, it is also possible to, preferably temporarily, only apply one of the steam heat integration options. This may happen, for example, if insufficient steam of the desired pressure or temperature is available, or when less duty of the primary or secondary guard bed heat exchanger is required.

In some embodiments, e.g. at start-up of the ethylene epoxidation process, when the ethylene oxide absorber overhead stream is not sufficiently hot, or during (temporary) by-pass of said absorber, the primary and/or secondary guard bed heat exchanger may at least partially replace the duty of the ethylene oxide absorber overhead (first) condenser. Alternatively, when the reactive absorber operates at a higher temperature than the normal operation temperature, more vapors are produced, leading to a higher recovered duty in the ethylene oxide absorber overhead condenser, and a reduced duty of the primary and/or secondary guard bed heat exchanger.

In some embodiments, if required, the primary and/or secondary guard bed heater, in order to at least partially replace the duty of the reactive absorber overhead condenser, may at least temporarily be operated using higher pressure (than normal) steam available in the process.

In other embodiments, the low-pressure steam used to operate the primary and secondary guard bed heater, obtained from the ethylene glycol purification column overhead condenser or produced by flashing collected process condensate streams, respectively, may (temporarily) at least partially be replaced or supplemented by low-pressure steam produced by cascading down high-pressure steam streams produced in the process. Examples of high-pressure steam producers in the process are the ethylene oxide reactor and the ethylene oxide reactor primary product cooler. In such case, the guard bed heaters sufficient have heat transfer area to (partially) replace the first EO absorber condenser duty.

In the process of the present invention, the heated recycle gas stream is contacted with one or more guard bed materials in one or more guard bed systems positioned upstream of an ethylene oxide reactor to provide a treated recycle gas stream.

In one embodiment, the one or more guard bed systems comprise a guard bed material capable of removing one or more alkyl iodide impurities from the recycle gas stream.

In another embodiment, the one or more guard bed systems comprise a guard bed material capable of removing a vinyl iodide impurity from the recycle gas stream.

In yet another embodiment, the one or more guard bed systems comprise a first guard bed material capable of removing one or more alkyl iodide impurities from the recycle gas stream and a second guard bed material capable of removing a vinyl iodide impurity from the recycle gas stream.

Typically, the process involves contacting the recycle gas stream with a first guard bed system comprising one or more guard bed vessels comprising a first guard bed material, and with a second guard bed system comprising one or more guard bed vessels comprising a second guard bed material.

Preferably, the process as disclosed herein comprises contacting at least a portion of the recycle gas stream in a first guard bed system comprising one or more guard bed vessels comprising a first guard bed material capable of removing one or more alkyl iodide impurities from the recycle gas stream to yield a partially treated recycle gas stream; and contacting at least a portion of the partially treated recycle gas stream in a second guard bed system comprising one or more guard bed vessels comprising a second guard bed material capable of removing a vinyl impurity from the recycle gas stream to provide a treated recycle gas stream.

Suitably, the guard bed material capable of removing one or more alkyl iodide impurities from the recycle gas stream comprises a first support material, and deposited on the first support material, silver in an amount of from 2% to 10% by weight. Suitably, the first support material may comprise alumina, titania, zirconia, silica, activated carbon, or any combination thereof. Preferably, the first support material comprises alumina, in particular gamma-alumina. A suitable first support material may have a surface area of more than 20 $m^2/g$, relative to the weight of the support material, or at least 25 $m^2/g$, or at least 50 $m^2/g$, or at least 75 $m^2/g$, or at least 100 $m^2/g$, or at least 125 $m^2/g$, or at most 1200 $m^2/g$, or at most 500 $m^2/g$, or at most 300 $m^2/g$, or at most 200 $m^2/g$, or at most 175 $m^2/g$, or from 20 $m^2/g$ to 1200 $m^2/g$, or from 50 $m^2/g$ to 500 $m^2/g$, or from 75 $m^2/g$ to 300 $m^2/g$, or from 100 $m^2/g$ to 200 $m^2/g$, or from 125 $m^2/g$ to 175 $m^2/g$, on the same basis. As used herein, "surface area" is understood to refer to the surface area of the support material as measured in accordance with the B.E.T. (Brunauer, Emmett and Teller) method as described in detail in Brunauer, S., Emmet, P. Y. and Teller, E., J. Am. Chem. Soc., 60, pgs. 309-316 (1938). Preferably, the first support material is a spherical support material and has a diameter of less than 2 mm, or 1.8 mm or less, or 1.6 mm or less, or 1.5 mm or less, or 1.3 mm or less, or 1.0 mm or less, or a diameter from 0.25 mm to less than 2 mm, or from 0.5 mm to less than 2 mm, or from 0.75 mm to less than 2 mm, or from 1 mm to less than 2 mm, or from 0.25 mm to 1.5 mm, or from 0.5 mm to 1.5 mm, or from 0.75 mm to 1.5 mm, or from 1 mm to 1.5 mm.

Preferably, the guard bed material capable of removing a vinyl iodide impurity from the recycle gas stream comprises a second support material, palladium and gold. Suitable second support materials are those comprising silica, alumina, silica-alumina, silica gel, silicic acid, silicates, silicon carbide, titania, zirconia, tungsten trioxide, pumice, magnesia, zeolites, and combinations thereof. Preferably, the second support material comprises silica, and may or may not further comprise alumina. In these embodiments, the silica content of the second support material may be at least 50 wt. %, more typically at least 90 wt. %, based on the weight of the support material. Frequently, the silica content of the second support material is at most 99.99 wt. %, more frequently at most 99.9 wt. %, on the same basis. Preferably, the second support material is in the form of particles or spheres having a diameter of from about 2 to 10 mm, or from 3 to 9 mm, or from 4 to 7 mm.

In a preferred embodiment, the process as disclosed herein comprises contacting at least a portion of a recycle gas stream comprising an alkyl iodide impurity and a vinyl iodide impurity in a first guard bed system comprising one or more guard bed vessels with a first guard bed material to yield a partially treated recycle gas stream, wherein the first guard bed material comprises a first support material, and deposited on the first support material, silver in an amount of from 2% to 10% by weight; and contacting at least a portion of the partially treated recycle gas stream in a second guard bed system comprising one or more guard bed vessels with a second guard bed material to yield a treated recycle gas stream, wherein the second guard bed material comprises a second support material, palladium and gold.

The second guard bed system configured for removing a vinyl impurity from the recycle gas stream as disclosed herein typically has a preferred operating temperature range that is lower than that of the first guard bed system configured for removing one or more alkyl iodide impurities from the recycle gas stream. Thus, in such case, the partially treated recycle gas stream leaving a first guard bed system for removing alkyl iodides impurities needs to be cooled to the preferred operating temperature range of the second guard bed system configured for removing a vinyl impurity from the recycle gas stream.

Preferably, the hot recycle gas stream leaving the one or more first guard bed systems for removing alkyl iodide impurities is cooled to a preferred temperature for supplying to one or more second guard bed systems for removing vinyl iodide impurities by means of water cooling.

As mentioned above, after treatment in one or more guard bed systems, and before being combined with the feed gas stream to the ethylene oxide reactor, the treated recycle gas stream is generally at least partially treated in a carbon dioxide removal section, to provide a carbon dioxide depleted recycle gas stream which may be recombined with any portion of the recycle gas stream bypassing the carbon dioxide removal section and then be recycled to the ethylene oxide reactor, where it contacted with the epoxidation catalyst.

The carbon dioxide removal section typically comprises a carbon dioxide absorber, wherein carbon dioxide is at least partially absorbed by a recirculating absorbent stream to produce a carbon dioxide-depleted overhead stream, and a carbon dioxide stripper for regenerating the saturated absorbent stream.

A temperature in the range of 40-80° C. is beneficial for absorption of carbon dioxide in the carbon dioxide absorber. Thus, the treated recycle gas stream leaving the one or more guard bed systems is advantageously cooled before being supplied to the carbon dioxide removal section.

Cooling of the recycle gas stream prior to carbon dioxide removal may be realized by heat exchange with the carbon dioxide absorber overhead stream, preferably in a shell-and-tube heat exchanger. Thus, prior to contacting it with the epoxidation catalyst in the ethylene oxide reactor, advantageously, the cooled, carbon dioxide depleted recycle gas stream leaving the carbon dioxide removal section is again heated by counter-currently contacting it with the hot treated recycle gas stream leaving the one or more guard bed systems. This is beneficial both in view of increased energy savings and because it allows reducing the duty of the downstream feed-product exchanger used for heating the recycle gas stream before feeding it to the ethylene oxide reactor.

Accordingly, in one embodiment, the treated recycle gas stream is supplied to a heat exchanger located upstream of the carbon dioxide removal section to produce a cooled treated recycle gas stream by heat exchange with the carbon dioxide absorber overhead stream, wherein said cooled treated recycle gas stream is supplied to a carbon dioxide removal section to produce a carbon dioxide depleted recycle gas stream.

Preferably, the carbon dioxide depleted recycle gas stream is further provided to a condenser to provide a cooled carbon dioxide-depleted recycle gas stream, wherein said cooled carbon dioxide-depleted recycle gas stream is again heated by heat exchange with the treated recycle stream in the heat exchanger upstream of the carbon dioxide removal section, to provide a heated carbon dioxide-depleted recycle gas stream. At least a portion of this stream is then, optionally after heating in feed product heat exchanger, contacted it with the epoxidation catalyst in the ethylene oxide reactor.

Preferably, the carbon dioxide removal section comprises a stripper reboiler, wherein heat is supplied to the carbon dioxide stripper reboiler by using at least a portion of the steam stream obtained from the ethylene glycol purification column overhead condenser or steam produced by flashing one or more condensate streams collected in the process, preferably steam obtained from the ethylene glycol purification column overhead condenser.

The present disclosure further relates to a reaction system for the production of ethylene carbonate and/or ethylene glycol comprising
(i) a recycle gas loop fluidly connected to a source of ethylene and oxygen;
(ii) an ethylene oxide reactor comprising an epoxidation catalyst, an inlet, and an outlet, wherein the inlet of the ethylene oxide reactor is fluidly connected to the recycle gas loop;
(iii) an ethylene oxide absorber configured to produce an ethylene oxide absorber overhead stream and a fat absorbent stream comprising ethylene carbonate and/or ethylene glycol, said ethylene oxide absorber comprising a carboxylation and hydrolysis catalyst, an inlet fluidly connected to the outlet of the ethylene oxide reactor, an inlet for lean absorbent, an outlet for discharging a recycle gas stream and an outlet for discharging a fat absorbent stream;
(iv) an ethylene oxide absorber overhead condenser configured to produce a recycle gas stream and a condensate stream, said ethylene oxide absorber overhead condenser comprising an inlet fluidly connected to the outlet of the ethylene oxide absorber for discharging a recycle gas stream, an inlet for receiving a cooled recycle gas stream, an outlet fluidly connected to the recycle gas loop, and an outlet for discharging a cooled recycle gas stream;
(v) a finishing reactor configured to produce an ethylene glycol stream, comprising an inlet fluidly connected to the outlet of the ethylene oxide absorber for discharging a fat absorbent stream, and an outlet for discharging an ethylene glycol stream;
(vi) a dehydrator configured to produce a concentrated ethylene glycol stream comprising an inlet and an outlet, comprising an inlet fluidly connected to the outlet for discharging an ethylene glycol stream from the finishing reactor, and an outlet for discharging a concentrated ethylene glycol stream;
(vii) an ethylene glycol purification column equipped with an ethylene glycol purification column overhead condenser, an inlet fluidly connected to outlet of the dehydrator for discharging a concentrated ethylene glycol stream, an outlet for discharging a condensate stream, and an outlet for discharging a steam stream,
(viii) one or more guard bed systems comprising an inlet, an outlet and one or more guard bed vessels comprising one or more guard bed materials, wherein the inlet of the guard bed system is fluidly connected to the recycle gas loop, wherein the one or more guard bed materials are configured to remove at least a portion of one or more impurities from the recycle gas stream to yield a treated recycle gas stream; and wherein the outlet of the guard bed system is fluidly connected to the recycle gas loop;
(ix) a guard bed heater located upstream of the one or more guard bed systems, comprising an inlet for receiving a recycle gas stream and outlet for discharging a heated recycle gas stream, wherein the guard bed heater is fluidly connected with the outlet of the ethylene glycol purification column overhead condenser for discharging a steam stream or with the steam outlet of a condensate flash vessel.

The benefits of the present disclosure are particularly pronounced if a specific succession of heat integration options is utilized for heating the recycle gas stream to the desired guard bed operating temperature, typically involving subsequent heat exchange with the ethylene oxide absorber overhead stream in the absorber overhead condenser; steam produced in an ethylene glycol purification column overhead condenser; and steam obtained by flashing one or more condensate streams collected in the process. Thus, preferably, the reaction system comprises a primary guard bed heater located upstream of the one or more guard bed systems, comprising an inlet for receiving a recycle gas stream and outlet for discharging a heated recycle gas stream, wherein the primary guard bed heater is fluidly connected with the outlet of the ethylene glycol purification column overhead condenser for discharging a steam stream; and a secondary guard bed heater located upstream of the one or more guard bed systems and downstream of the primary guard bed heater, comprising an inlet for receiving a heated recycle gas stream and outlet for discharging a further heated recycle gas stream, wherein the secondary guard bed heater is fluidly connected with the steam outlet of a condensate flash vessel.

As noted previously, in order to achieve sufficient deep cooling for condensation of the ethylene absorber overhead stream, typically a second condenser is used downstream of the of the ethylene oxide absorber overhead condenser. Accordingly, in a preferred embodiment, the system further comprises a condenser located downstream of the ethylene oxide absorber overhead condenser, comprising an inlet fluidly connected to the outlet of the ethylene oxide absorber overhead condenser for discharging a cooled recycle gas stream, and an outlet for discharging a cooled recycle gas stream.

Preferably, the reaction system further comprises a carbon dioxide removal section fluidly connected to the recycle gas loop, as described in detail above. Typically, such a carbon dioxide removal section comprises a carbon dioxide stripper comprising a carbon dioxide stripper reboiler, wherein said reboiler is heated by heat integration with a hot process stream withdrawn from the reaction system, preferably steam from an ethylene glycol purification column overhead condenser or steam obtained by flashing collected condensate streams.

Figure 1:
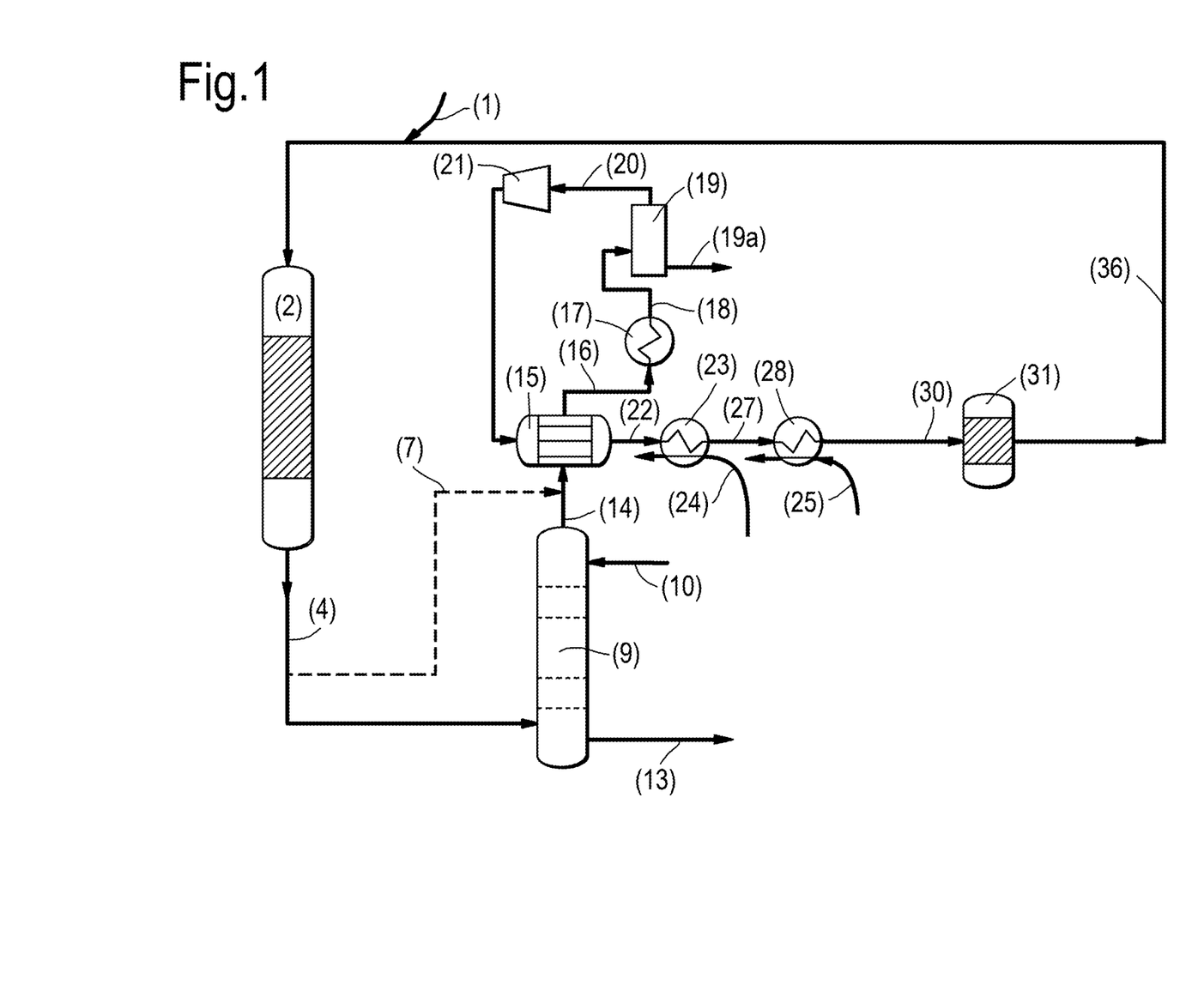
FIGS. 1 and 2 are schematic illustrations showing exemplary, but non-limiting embodiments of the present disclosure.
Figure 2:
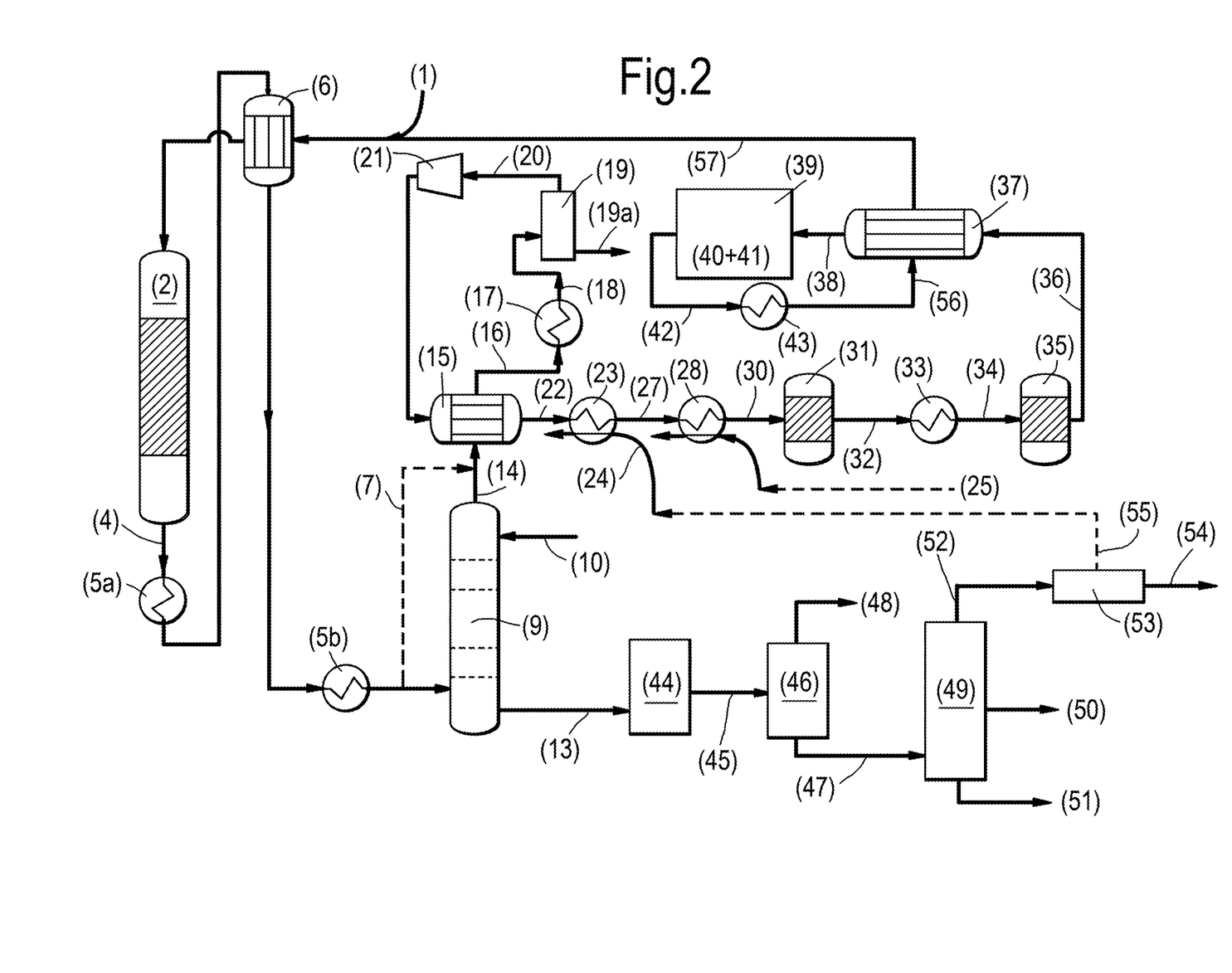

Reference is now made to FIGS. 1 and 2, which are schematic views of a reaction system for the production of ethylene carbonate and/or ethylene glycol, according to an embodiment of the present disclosure. It will be clear to the skilled person, that as schematic diagrams these figures do not show all necessary inputs, outputs, recycle streams, etc. that may be present in the reaction system.

Furthermore, in the figures herein, as will be appreciated, elements can be added, exchanged, and/or eliminated so as to provide any number of additional embodiments and the sequence in which various feed components and/or streams are introduced into the process and their respective points of introduction, as well as the flow connections, may be varied from that depicted. In addition, as will be appreciated, the proportion and the relative scale of the elements provided in the figure are intended to illustrate the embodiments of the present disclosure, and should not be taken in a limiting sense.

As shown in FIG. 1, the reaction system includes ethylene oxide reactor (2), which comprises an epoxidation catalyst. Epoxidation feed gas (1) is supplied to ethylene oxide reactor (2) via one or more inlets, and typically comprises ethylene, oxygen, ballast gas (e.g., methane or nitrogen), and a reaction modifier (e.g., monochloroethane, vinyl chloride or dichloroethane). In ethylene oxide reactor (2), ethylene is reacted with oxygen in the presence of an epoxidation catalyst to yield ethylene oxide product stream (4). Ethylene oxide product stream (4) exits ethylene oxide reactor (2), and to an inlet of absorber (9).

In absorber (9), the ethylene oxide product stream is brought into intimate contact with lean absorbent, supplied via line (10), in the presence of one or more carboxylation and hydrolysis catalysts. At least a portion of, and preferably substantially all of, the ethylene oxide in the ethylene oxide product stream is absorbed into the lean absorbent. Fat absorbent stream (13), which comprises ethylene carbonate and/or ethylene glycol, is withdrawn from absorber (9) via an outlet. Any gases not absorbed in absorber (9) are withdrawn as hot ethylene absorber overhead stream, which is at least partially supplied as stream (14) to a condenser (15) to yield cooled absorber overhead stream (16). Cooled overhead absorber stream (16) is typically further cooled in a secondary condenser (17), e.g. using water cooling, to provide a further cooled overhead absorber stream (18). The further cooled overhead absorber stream (18) is supplied to a suitable vapor-liquid separator (19) (such as a knock-out vessel, an absorber knock-out column including a wash section etc.) to yield cooled and dehydrated recycle gas stream (20) and aqueous stream (19*a*). Cooled recycle gas stream (20) is typically compressed using compressor (21) and supplied to condenser (15). Condenser (15) as shown herein is an integrated condenser for counter-currently cooling hot stream (14) and heating cooled recycle stream (20), to provide heated recycle gas stream (22). Heated recycle gas stream (22) may be further heated to the preferred guard bed system operating temperature in a heat exchanger ["guard bed heater"] (23) or (28), or typically multiple heat exchangers, upstream of the guard bed system(s), in order to produce further heated recycle gas streams (27) and (30). The thermal energy needed for the operation of the one or more guard bed heaters may be supplied by heat integration with low-pressure steam produced elsewhere in the process, such as steam from monoethylene glycol (MEG) purification column overhead condenser supplied via line (24), or steam obtained by flashing the combined condensates collected from steam consumers in the process, supplied via line (25), or preferably, as shown in FIG. 1, a combination of a primary guard bed heater (23) using low-pressure steam from monoethylene glycol (MEG) purification column overhead condenser supplied via line (24) and a secondary guard bed heater (28) using slightly higher pressure steam obtained by flashing the combined condensates collected from steam consumers in the process, supplied via line (25).

Heated recycle gas stream (30) is brought into contact with a packed bed of a guard bed material in a guard bed system (31) comprising one or more guard bed vessels, wherein said guard bed material is capable of removing gaseous iodide impurities from the recycle gas stream. By contacting heated recycle gas stream (30) with the guard bed material, at least a portion of the iodide impurities are removed from recycle gas stream (30) to yield a treated recycle gas stream (36), which comprises a reduced amount of the iodide impurities relative to recycle gas stream (30). At least a portion of treated recycle gas stream (36) is combined with feed gas stream (1) and supplied to ethylene oxide reactor (2).

Also shown in FIG. 1 as dashed line (7) is a by-pass of absorber (9) by directly providing EO reactor effluent stream (4) containing no EO (for example during start-up) and when the EO absorber is out of operation, as gaseous stream to condenser (15). In such case, the feed stream to condenser (15) is generally cooler than ethylene absorber overhead stream (14), thus requiring additional heating duty of heat exchanger (23) (or any additional heaters upstream of the guard bed system(s)).

In addition to the components shown in FIG. 1, the reaction system in FIG. 2 includes feed product exchanger (6) for counter-currently heating recycle gas stream (57) provided to ethylene oxide reactor (2), as well as a primary product cooler (5*a*) and secondary product cooler (5*b*). In the system of FIG. 2, the thermal energy needed for the operation of guard bed primary heater (23) is preferably supplied by heat integration with low-pressure steam [typically 0.15-0.25 MPa gauge] from monoethylene glycol (MEG) purification column overhead condenser supplied via line (24). The further heated recycle gas stream (27) that leaves guard bed primary heater (23) is further heated in guard bed secondary heater (28), which is preferably heated by heat integration with low-pressure steam [typically 0.25-0.34 MPa gauge] supplied via line (25), obtained by flashing collected condensates in the process. Preferably, in guard bed system (31) at least a portion of the alkyl iodide impurities present in recycle gas stream (30) are removed to yield partially treated recycle gas stream (32), which comprises a reduced amount of alkyl iodide impurities relative to recycle gas stream (30). At least a portion of partially treated recycle gas stream (32) may be supplied to guard bed cooler (33), wherein recycle gas stream (32) is typically cooled by cooling water to the desired operating temperature of second guard bed system (35). Cooled, partially treated, recycle gas stream (34) leaves guard bed cooler (33) and may be supplied to a second guard bed system (35), wherein partially treated recycle gas stream (34) is brought into contact with a packed bed of a second guard bed material in a guard bed vessel, wherein said second guard bed material is preferably capable of removing a vinyl iodide impurity from the recycle gas stream. By contacting partially treated recycle gas stream (34) with the second guard bed material, preferably at least a portion of the vinyl iodide impurity is removed from partially treated recycle gas stream (34) to yield treated recycle gas stream (36), which comprises a reduced amount of the vinyl iodide impurity relative to recycle gas stream (34). Treated recycle gas stream (36) exits second guard bed system (35) and is supplied to guard bed product heat exchanger (37). Herein, treated recycle gas stream (36) is cooled, by heat exchange with the carbon dioxide absorber overhead stream, to provide a cooled treated recycle gas stream (38) having a temperature corresponding to the preferred operating temperature of carbon dioxide removal section (39) which is in fluid communication with the recycle gas loop. Carbon dioxide removal section (39) typically comprises a carbon dioxide absorber (40) and a carbon dioxide stripper equipped with a carbon dioxide stripper reboiler (41) (details not shown). Optionally, the carbon dioxide stripper reboiler is heated by heat integration with a hot process stream withdrawn from the reaction system, preferably steam supplied via line (24) withdrawn as stream (55) from the ethylene glycol purification column overhead condenser or steam supplied via line (25) obtained by flashing collected process condensate streams.

A carbon dioxide-depleted recycle gas stream (42) exits carbon dioxide removal section (39), and is preferably provided to a condenser (43) and a vapor-liquid separator (such as a knock-out vessel; not shown) to provide a further cooled stream overhead stream (56). This carbon-dioxide depleted recycle gas stream (56) may be heated by countercurrently contacting it in guard bed product stream heat exchanger (37) with treated recycle gas stream (36) to provide a heated treated, carbon dioxide-depleted recycle gas stream (57), of which at least a portion is combined with feed gas stream (1), fed through feed-product exchanger (6) and subsequently supplied to ethylene oxide reactor (2).

In the system shown in FIG. 2, a fat absorbent stream (13) obtained as bottoms stream from absorber (9), comprising ethylene carbonate and/or ethylene glycol, is supplied to one or more finishing reactors, such as hydrolysis reactor (44) (e.g., to provide further conversion of any ethylene oxide and/or ethylene carbonate that was not converted in the ethylene oxide absorber). Finishing reactor product stream (45) is withdrawn from the one or more finishing reactors, such as hydrolysis reactor (44), and supplied to dehydrator (46). In dehydrator (46), water is removed from the dehydrator feed stream to yield dehydrator bottom stream (47) comprising predominantly MEG, and overhead dehydrator stream (48).

Dehydrator bottom stream (47) is withdrawn from dehydrator (46) and optionally supplied to a monoethylene glycol purification column (49) to provide a purified MEG stream (50) and a bottom stream (51), which may be recycled as lean absorbent stream (10) to absorber (9). Monoethylene glycol purification column overhead stream (52) is supplied to monoethylene glycol purification column condenser (53) to provide condensate stream [54] (which is typically used, with partial bleed as pasteurization cut, as reflux back to the purification column) and low-pressure steam stream (55) which may be utilized for heat integration through line (24) with primary guard bed heater (23). In some embodiments, any surplus steam produced in monoethylene glycol purification column condenser (53) may be used to provide heat to the reboiler of carbon dioxide stripper (41) (not shown).

That which is claimed is:

1. A process comprising
    supplying an ethylene oxide absorber overhead stream (14) to a condenser (15) to produce a cooled recycle gas stream (20) and one or more aqueous streams,
    heating at least a portion of said cooled recycle gas stream (20) to provide a heated recycle gas stream (30),
    contacting said heated recycle gas stream (30) with one or more guard bed materials in one or more guard bed systems (31) positioned upstream of an ethylene oxide reactor (2) to provide a treated recycle gas stream (36),
    contacting an epoxidation feed gas (1) comprising ethylene, oxygen and at least a portion of said treated recycle gas stream (36) with an epoxidation catalyst in ethylene oxide reactor (2) to yield an epoxidation reaction product stream (4),
    contacting the epoxidation reaction product stream (4) in an ethylene oxide absorber (9) with a lean absorbent stream (10) in the presence of a carboxylation and hydrolysis catalyst to yield a fat absorbent stream (13) comprising ethylene carbonate and/or ethylene glycol and an ethylene oxide absorber overhead stream (14),
    wherein cooled recycle gas stream (20) is heated by heat exchange with a hot process stream selected from
    (i) the ethylene oxide absorber overhead stream (14), in a condenser (15);
    (ii) steam (24) produced in an ethylene glycol purification column overhead condenser, in a first heat exchanger located downstream of condenser (15);
    (iii) steam (25) produced by flashing one or more condensate streams collected in the process, in a second heat exchanger located downstream of condenser (15), or a combination thereof.

2. The process according to claim 1, wherein ethylene oxide absorber overhead stream (14) is provided to a first condenser (15) to produce a dewatered recycle gas stream (16) and an aqueous stream,
    wherein dewatered recycle gas stream (16) is supplied to a second condenser (17) to produce a further dewatered and cooled recycle gas stream (18), and
    wherein recycle gas stream (18) is supplied to a vapor-liquid separator (19) to produce cooled and dehydrated recycle gas stream (20).

3. The process according to claim 2 further comprising supplying at least a portion of fat absorbent stream (13) comprising ethylene carbonate and/or ethylene glycol to one or more finishing reactors (44) and/or one or more dehydrators (46) to provide a concentrated ethylene glycol stream (47), supplying at least a portion of the concentrated ethylene glycol stream (47) to an ethylene glycol purification column (49) to produce a purified ethylene glycol stream (50) and a vaporous overhead stream (52), and supplying said vaporous overhead stream (52) to an ethylene glycol purification column overhead condenser (53) to produce a condensate stream (54) and a steam stream (55).

4. The process according to claim 1, wherein the cooled recycle gas stream (20) is heated by subsequent heat exchange with the ethylene oxide absorber overhead stream (14) in condenser (15); steam (24) produced in an ethylene glycol purification column overhead condenser; and steam (25) obtained by flashing one or more condensate streams collected in the process.

5. The process according to claim 1,
wherein the treated recycle gas stream (36) is supplied to a heat exchanger (37) to produce a cooled treated recycle gas stream (38),
wherein said cooled treated recycle gas stream (38) is supplied to a carbon dioxide removal section (39) to produce a carbon dioxide depleted recycle gas stream (42).

6. The process according to claim 5, wherein the carbon dioxide depleted recycle gas stream (42) is provided to a condenser to provide a cooled carbon dioxide depleted recycle gas stream (56),
wherein stream (56) is heated by heat exchange with the treated recycle stream (36) in heat exchanger (37) to provide a heated carbon dioxide-depleted recycle gas stream (57).

7. The process according to claim 6, wherein the carbon dioxide removal section (39) comprises a carbon dioxide absorber (40) and a carbon dioxide stripper equipped with a carbon dioxide stripper reboiler (41),
wherein heat is supplied to the carbon dioxide stripper reboiler by using at least a portion of the steam stream (55) obtained from the ethylene glycol purification column overhead condenser (53) or steam produced by flashing one or more condensate streams collected in the process.

8. The process according to claim 1, wherein the one or more guard bed systems comprise a guard bed material capable of removing one or more alkyl iodide impurities from the recycle gas stream and/or a guard bed material capable of removing a vinyl iodide impurity from the recycle gas stream.

9. The process according to claim 8, comprising
contacting at least a portion of a recycle gas stream comprising an alkyl iodide impurity and a vinyl iodide impurity with a first guard bed material in first guard bed system to yield a partially treated recycle gas stream, wherein the first guard bed material comprises a first support material, and deposited on the first support material, silver in an amount of from 2% to 10% by weight; and
contacting at least a portion of the partially treated recycle gas stream with a second guard bed material in a second guard bed system to yield a treated recycle gas stream, wherein the second guard bed material comprises a second support material, palladium and gold.

10. A reaction system for the production of ethylene carbonate and/or ethylene glycol comprising
(i) a recycle gas loop fluidly connected to a source (1) of ethylene and oxygen;
(ii) an ethylene oxide reactor (2) comprising an epoxidation catalyst, an inlet, and an outlet, wherein the inlet of the ethylene oxide reactor is fluidly connected to the recycle gas loop;
(iii) an ethylene oxide absorber (9) configured to produce an ethylene oxide absorber overhead stream and a fat absorbent stream comprising ethylene carbonate and/or ethylene glycol, said ethylene oxide absorber (9) comprising a carboxylation and hydrolysis catalyst, an inlet fluidly connected to the outlet of the ethylene oxide reactor, an inlet (10) for lean absorbent, an outlet for discharging a recycle gas stream (14) and an outlet for discharging a fat absorbent stream (13);
(iv) an ethylene oxide absorber overhead condenser (15) configured to produce a recycle gas stream and a condensate stream, said ethylene oxide absorber overhead condenser comprising an inlet fluidly connected to the outlet of the ethylene oxide absorber (9) for discharging a recycle gas stream, an inlet for receiving a cooled recycle gas stream, an outlet fluidly connected to the recycle gas loop, and an outlet for discharging a cooled recycle gas stream (22);
(v) a finishing reactor (44) configured to produce an ethylene glycol stream, comprising an inlet fluidly connected to the outlet of the ethylene oxide absorber for discharging a fat absorbent stream (13), and an outlet for discharging an ethylene glycol stream (45);
(vi) a dehydrator (46) configured to produce a concentrated ethylene glycol stream comprising an inlet and an outlet, comprising an inlet fluidly connected to the outlet for discharging an ethylene glycol stream (45) from the finishing reactor (44), and an outlet for discharging a concentrated ethylene glycol stream (47);
(vii) an ethylene glycol purification column (49) equipped with an ethylene glycol purification column overhead condenser (53), an inlet fluidly connected to outlet of the dehydrator for discharging a concentrated ethylene glycol stream (47), an outlet for discharging a condensate stream (54), and an outlet for discharging a steam stream (55),
(viii) one or more guard bed systems (31), (35) comprising an inlet, an outlet and one or more guard bed vessels comprising one or more guard bed materials, wherein the inlet of the guard bed system is fluidly connected to the recycle gas loop, wherein the one or more guard bed materials are configured to remove at least a portion of one or more impurities from the recycle gas stream to yield a treated recycle gas stream (36); and wherein the outlet of the guard bed system is fluidly connected to the recycle gas loop;
(ix) one or more guard bed heaters (23),(28), (33) located upstream of the one or more guard bed systems, comprising an inlet for receiving a recycle gas stream and outlet for discharging a heated recycle gas stream, wherein the one or more guard bed heaters are fluidly connected with the outlet of the ethylene glycol purification column overhead condenser for discharging a steam stream (55) and/or with the steam outlet of a condensate flash vessel.

11. The reaction system according to claim 10, comprising
a primary guard bed heater (23) located upstream of the one or more guard bed systems, comprising an inlet for receiving a recycle gas stream and outlet for discharging a heated recycle gas stream (27), wherein the primary guard bed heater is fluidly connected with the outlet of the ethylene glycol purification column overhead condenser for discharging a steam stream (55); and a secondary guard bed heater (28) located upstream of the one or more guard bed systems and downstream of the primary guard bed heater (23), comprising an inlet for receiving a heated recycle gas stream (27) and outlet for discharging a further heated recycle gas stream (30), wherein the secondary guard bed heater is fluidly connected with the steam outlet of a condensate flash vessel.

12. The reaction system according to claim 10, further comprising a condenser (17) located downstream of the ethylene oxide absorber overhead condenser, comprising an inlet fluidly connected to the outlet of the ethylene oxide absorber overhead condenser for discharging a cooled recycle gas stream (22), and an outlet for discharging a further cooled recycle gas stream (20).

13. The reaction system according to claim 10, further comprising a carbon dioxide removal section fluidly connected to the recycle gas loop, wherein said carbon dioxide removal section comprises a carbon dioxide absorber (40) and a carbon dioxide stripper (41).

14. The reaction system according to claim 13, comprising a heat exchanger (37) located upstream of the carbon dioxide removal section, wherein said heat exchanger comprises and inlet for receiving a treated recycle gas stream (36) and an inlet for receiving a carbon dioxide absorber overhead stream (56), an outlet for discharging a cooled treated recycle gas stream (38) and an outlet for discharging a heated carbon dioxide-depleted recycle gas stream (57), wherein said heat exchanger is configured to exchange heat between treated recycle gas stream (36) and carbon dioxide absorber overhead stream (56).

15. The reaction system according to claim 13, wherein the carbon dioxide removal section comprises a carbon dioxide stripper comprising a carbon dioxide stripper reboiler, wherein said reboiler is heated by heat integration with a hot process stream withdrawn from the reaction system, preferably steam (55) from an ethylene glycol purification column overhead condenser (53) or steam obtained by flashing collected condensate streams.

* * * * *